United States Patent [19]

Christiansen et al.

[11] 4,398,277
[45] Aug. 9, 1983

[54] CONDUCTIVE ELASTOMERIC FABRIC AND BODY STRAP

[75] Inventors: Robert W. Christiansen, Clayton Township, Polk County, Wis.; Walter M. Westberg, St. Paul, Minn.

[73] Assignee: Minnesota Mining and Manufacturing Company, Saint Paul, Minn.

[21] Appl. No.: 286,766

[22] Filed: Jul. 27, 1981

[51] Int. Cl.³ .............................................. H05F 3/02
[52] U.S. Cl. ..................................... 361/220; 57/901; 361/212
[58] Field of Search ............... 361/212, 220, 224, 223; 174/5 R, 5 G; 128/385, 388, 389, 796, 798, 799, 802, 804; 2/162, 170; 57/901

[56] References Cited

U.S. PATENT DOCUMENTS

| | | | |
|---|---|---|---|
| 3,422,460 | 1/1969 | Burke et al. ...................... | 57/901 X |
| 3,424,698 | 1/1969 | Lupinski et al. | |
| 3,541,389 | 11/1970 | Van Name .......................... | 361/224 |
| 3,582,448 | 6/1971 | Okuhashi et al. .................. | 57/901 X |
| 3,699,590 | 10/1972 | Webber et al. ................... | 361/220 X |
| 3,904,929 | 9/1975 | Kanaya et al. | |
| 3,987,613 | 10/1976 | Woods et al. | |
| 4,267,233 | 5/1981 | Tanaka et al. | |
| 4,321,789 | 3/1982 | Dammann et al. ................ | 57/901 X |

FOREIGN PATENT DOCUMENTS

| | | | |
|---|---|---|---|
| 2547390 | 5/1977 | Fed. Rep. of Germany ...... | 361/212 |
| 1067260 | 5/1967 | United Kingdom . | |

*Primary Examiner*—Harry E. Moose, Jr.
*Attorney, Agent, or Firm*—Cruzan Alexander; Donald M. Sell; William D. Bauer

[57] ABSTRACT

A fabric and body strap having both electrically conductive and elastomeric properties. A fabric is formed by interlacing at least one yarn into a series of interlocking loops and preferably knitted. The yarn includes an end having an electrically conductive fiber and an end having an elastomeric fiber. It is preferred that an electrically conductive yarn and an insulative yarn are interlaced together to form a series of interlocking loops. The electrically conductive yarn includes an end having an electrically conductive fiber and the insulative yarn includes an end having an insulative fiber. Either one or both of the electrically conductive fiber and the insulative fiber is plaited with an end having an elastomeric fiber. The electrically conductive yarn and the insulative yarn may be knit together on two levels forming a face and a back with the electrically conductive yarn forming interlocking loops on the face while the insulative yarn forms interlocking loops on both the face and back. Electrical and mechanical connectors, either separate or combined, form the fabric into a body strap.

15 Claims, 4 Drawing Figures

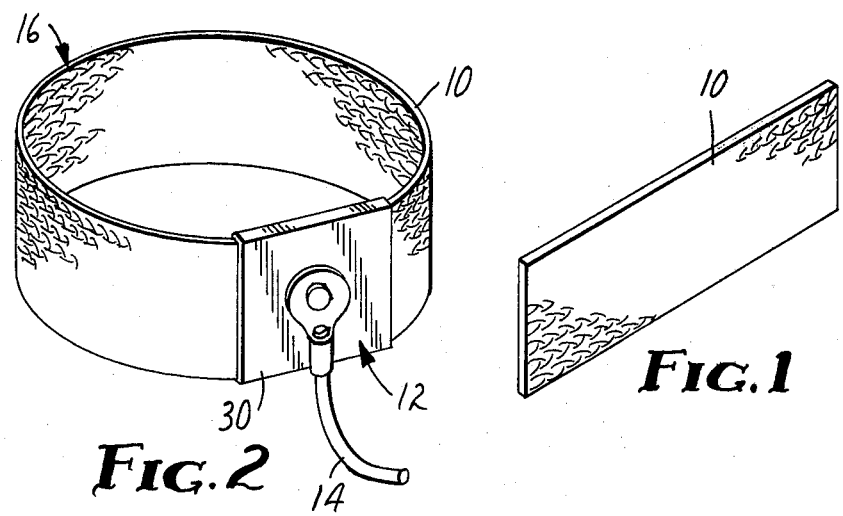
Fig. 1
Fig. 2
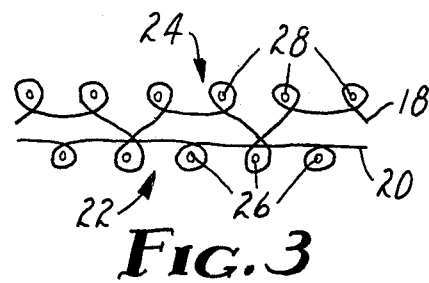
Fig. 3
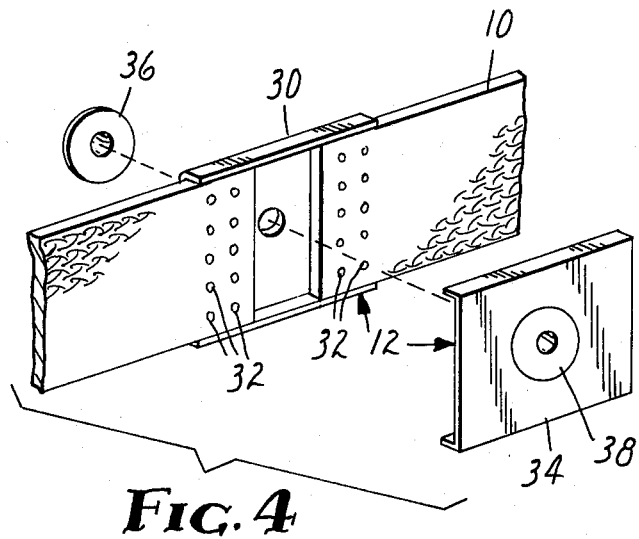
Fig. 4

CONDUCTIVE ELASTOMERIC FABRIC AND BODY STRAP

BACKGROUND OF THE INVENTION

The present invention relates generally to antistatic devices and more particularly to a fabric and body strap having both conductive and elastomeric properties.

Generally a need exists for devices to control the elastrostatic charge accumulation on the body or person of an individual. Certain individuals occupy areas or handle materials in which an electrostatic discharge could either be hazardous to the individual or could damage the material being handled. Examples are individuals in the proximity of an explosive or hazardous environment and individuals who must handle static sensitive electronic components.

Many devices have been developed to solve the problem of electrostatic charge accumulation and subsequent discharge. These include devices which have been fashioned into body straps or wrist straps to be worn by the particular individual involved. These body straps or wrist straps are then adapted to be connected to a ground potential, possibly through a predetermined resistance, in order to dissipate the electrostatic charge accumulation on the individual and to prevent additional electrostatic charge accumulation. These devices operate by draining off any accumulated electrostatic charge from the individual.

One of these devices is the Model 2064 wrist strap manufactured by Minnesota Mining and Manufacturing Company (3M), St. Paul, Minn. The Model 2064 wrist strap consists of a Velostat (Velostat is a trademark of the 3M Company) strip held on the wrist with a band of nylon. Velostat conductive material is a carbon loaded conductive polymer. The operation of the wrist strap relies on the conductive polymer to conduct electrostatic charge via the individual's wrist to a ground cord secured to the wrist strap with an electrically conductive snap connection. The wrist strap relies on a hook and loop fastener system (e.g. Scotchmate, a trademark of 3M, fastener or Velcro, a trademark of Velcro U.S.A., Inc., Manchester, New Hampshire, fastener) to secure the wrist strap to the wrist of the individual wearer.

A wrist strap manufactured by Semtronics Corporation, Peach Tree City, Ga. is constructed from similar functional components. The Semtronics wrist strap also uses a black conductive plastic secured to the wrist with a hook and loop closure system.

A wrist strap manufactured by Simco, Landsdale, Penna., also uses a similar system. The entire band of the wrist strap is made of a nylon hook and loop fastener system. The Simco wrist strap has a carbon loaded conductive material secured to the inner surface of the hook and loop fastener. A snap connection is provided for a ground cord. The Simco wrist strap again relies on the conductive polymer for conducting the electrostatic accumulation on the individual to the snap connection and to the grounding cord. Similarly, the Simco wrist strap also relies on the hook and loop fastener for the closure system.

A wrist strap manufactured by Wescorp of Mountain View, Calif. consists of a carbon loaded conductive fabric with a hook and loop fastener. The Wescorp wrist strap relies on the conductive fabric for the conduction of electrostatic charge from the individual instead of the conductive polymer as in the previous straps but again relies on the hook and loop fastener for the closure system. The Wescorp strap also utilizes the conductive fabric for a connection to ground rather than a connection point to a ground wire.

A strap manufactured by Walter G. Legge Company, New York, N. Y., carrying the name "WRISTSTAT" uses a black nylon band with a hook and loop fastener. A conductive polymer is attached to the band with a metallic plate at a relatively narrow location around the strap. The conductive polymer also has a snap connection to a ground cord. The Legge wrist strap relies on the metal plate and the conductive polymer for conductivity and relies on the nylon band with the hook and loop fastener for the closure system.

The straps heretofore described are all very similar in nature. Almost all rely on a carbon loaded conductive polymer and the remainder on a carbon loaded fabric. All of the wrist straps rely on a hook and loop fastener for a closure system. The use of a carbon loaded conductive material, while electrically functional, yields a structure black in color which is aesthetically not appealing. Although it must be noted that the Simco wrist strap limits the black color to the interior surface of the nylon band which otherwise can be colored as desired. Most importantly, however, all of the wrist straps rely on a closure system which is detachable and needs to be adjusted by the individual wearer. All of the straps rely on the firmly intimate contact of a conductive member to the body or person of the individual. A detachable and adjustable closure system must be adjusted individually by the wearer each time the strap is put on. Proper adjustment is required for proper functioning of the strap. This adjustability necessarily means that since it can be adjusted properly it can also be adjusted improperly. Proper functioning then demands that the wearer be trained and skilled in the proper adjustment and have the incentive to adjust the strap properly every time it is worn. In any event, the wearer's supervisors can never be sure of proper installation and proper performance consistently. Particularly in an area where sensitive electronic components are being handled, the result may be a degradation of component reliability since the improper adjustment and loss of function of the strap may result in damage to the sensitive electronic components which may not become apparent until installed and used by the ultimate customer of those components.

Wescorp also has a strap consisting of a metallic bead chain to which an electrical ground cord is slideably attached. The strap relies on the metallic beads for conductivity. Since it is worn loosely around the wrist, it can be made large enough to slip over the hand onto the wrist and thus no detachable closure is required. This strap however does suffer from the same improper adjustment problems of previous straps since its electrical connection is not ensured since the strap does not intimately contact the body (wrist) of the individual wearer.

Controlled Static Company, Santa Fe, Calif. manufactures a wrist strap known in the trade as a Fred strap. The strap is a metallic expansion band having a snap connection for an electrical ground cord. The band is reminiscent of a metallic expansion watchband. The band relies on the conductivity of the metal for the drainage of the accumulated electrostatic charges and will expand to slip on the wrist over the hand and then fit relatively snugly. However, the wrist strap suffers the disadvantage of a relatively low expansion ratio.

The strap must be large enough to slip over the hand, yet small enough to fit snugly on the wrist.

The two previous metallic straps also suffer another significant disadvantage. Since the highly conductive metallic surface is available at the outside surface of the wrist strap, there is a danger of accidental contact with a high voltage source and the resultant "welding" of the strap to that source preventing disengagement of the wearer from the high voltage source. It is for this reason that some electricians do not wear metallic rings, bracelets and other jewelry.

SUMMARY OF THE INVENTION

The present invention solves the problems with the prior conductive straps. A fabric is provided by interlacing at least one yarn. The yarn has an end having an electrically conductive fiber and an end having an elastomeric fiber. It is contemplated that the interlacing of the yarn includes an interlacing to form a series of interlocking loops and preferably where the interlacing is a knitting operation.

In a preferred embodiment, the fabric includes an electrically conductive yarn and an insulative yarn, interlaced together to form a series of interlocking loops. The electrically conductive yarn includes an end having an electrically conductive fiber and the insulative yarn includes an end having an insulative fiber. Either one or both of the electrically conductive fiber and the insulative fiber is plaited with an end having an elastomeric fiber. The result is a fabric which has both electrical conductivity and excellent elasticity. In a preferred embodiment the fabric is constructed where the electrically conductive yarn and the insulative yarn are knitted together to form a face and back. The insulative yarn then forms interlocking loops on both the face and the back while the electrically conductive yarn forms interlocking loops on said face.

The fabric may then be constructed into a conductive body strap by means of a mechanical connection coupled to the fabric forming the fabric into a closed loop with an inside electrically conductive surface adapted to contact the body. An electrical connection is then coupled to the fabric for contacting the electrically conductive fiber and providing a connection point for an electrical cable capable of electrically connecting the body strap to ground.

A fabric or body strap so constructed has superior performance characteristics over those illustrated in the prior art. It is surprising that the fabric so constructed which contains a relatively non-elastomeric metallic fiber will have the desired elasticity characteristics when interlaced or knitted with an elastomeric fiber. Further, the fabric provides a strap which does not need a detachable and adjustable closure system. The strap constructed of the fabric has a sufficient elasticity to slip over the hand and fit snug on the wrist without an individual adjustment each time a new wearer is fitted with a new strap. The fabric can be constructed into a strap which needs no adjustment by the individual, and hence the individual cannot put it on wrong with the resulting improper function. This gives assurance to the supervisor of the proper function of the strap and assures that product quality is not downgraded due to the lack of functionality of the strap. The strap is lightweight, flexible, comfortable, and the knitted fabric breathes preventing unacceptable heat and moisture buildup. When the fabric is knitted into two layers, the fabric also provides an exterior surface which is relatively insulative, and which will not "weld" upon an accidental contact with a high voltage potential.

BRIEF DESCRIPTION OF THE DRAWINGS

The foregoing advantages, construction and operation of the present invention will become more readily apparent from the following description and accompanying drawings in which:

FIG. 1 is a perspective view of the completed fabric;

FIG. 2 is a perspective view of the fabric completed into a strap with an electrical ground cord connected;

FIG. 3 is an end cross-sectional view of the fabric showing a preferred interlacing; and FIG. 4 is an explosion of the mechanical and electrical connector.

DESCRIPTION OF THE PREFERRED EMBODIMENTS

FIG. 1 shows a perspective view of the conductive and elastic fabric 10. The fabric 10 has at least one interlaced yarn preferably interlaced together to form a series of interlocking loops and still preferably knitted together. The one yarn has an end of an electrically conductive fiber and an end of an elastomeric fiber. The fabric 10 can also have two yarns and this construction is generally preferred. With two yarns, one yarn can be an electrically conductive yarn and the second yarn can be an insulative yarn. Again, the electrically conductive yarn and the insulative yarn are interlaced together to form a series of interlocking loops and preferably knitted together. The insulative yarn includes an end having an insulative fiber and the electrically conductive yarn has an end having an electrically conductive fiber. Either or both of the ends having an electrically conductive fiber and the end having an insulative fiber are plaited with an end having an elastomeric fiber.

In a preferred embodiment, the fabric is knit together utilizing an electrically conductive yarn and an insulative yarn. The insulative yarn contains an end having an insulative fiber plaited with an end having an elastomeric fiber. The electrically conductive yarn contains an end having an electrically conductive fiber plaited with an end also having an elastomeric fiber. In particular, the insulative yarn consists of 200 denier texturized nylon plaited over 184 denier bare spandex. Spandex as defined in Whittington's Dictionary of Plastics, First Edition, 1968, sponsored by the Society of Plastics Engineers, Incorporated, and published by the Technomic Publishing Company, Incorporated, 750 Summer Street, Stanford, Conn., is a generic name for a manufactured fiber in which the fiber-forming substance is a long chain synthetic polymer comprised of at least 85% of a segmented polyurethane. The electrically conductive yarn more particularly consists of two ends of Bekitex (Bekitex is a trademark of Baekert, Belgium) BK 50/1 yarn plaited over 184 denier bare spandex. Bekitex BK yarn is manufactured by Baekert of Belgium and consists of a yarn containing polyester fibers and a multiplicity of staple stainless steel fibers. The Bekitex BK yarn is described generally in U.S. Pat. No. 3,987,613, which is hereby incorporated by reference.

It is significant that the fabric 10 is interlaced to form a knitted structure and is not woven.

FIG. 2 shows a perspective view of the fabric 10 formed into a closed loop by a connector 12. The connector 12 provides both the mechanical connection closing the fabric 10 into the closed loop and also provides the electrical connection from the ground cord 14 to the electrically conductive fibers of the fabric 10. The body strap 16 consists of both the fabric 10 and the connector 12. Although not required, it is preferred that the body strap 16 not be coupled to ground directly with ground cord 14, but be coupled in series through a predetermined resistance, preferably approximately 1 megohm. In the case of an accidental contact of the ground cord 14 to a voltage source or in the case of an accidental contact of the wearer to a line voltage, the presence of such a resistance would help prevent electrical shock injury to the wearer of the body strap 16.

FIG. 3 represents an end view of a cross section of the fabric 10 showing the preferred knit structure of the fabric 10. FIG. 3 shows insulative yarn 18 and electrically conductive yarn 20. Insulative yarn 18 and electrically conductive yarn 20 are being knit together on two levels to form a face 22 and a back 24. The insulative yarn 18 forms a series of interlocking loops on both the face 22 and the back 24. Electrically conductive yarn 20 forms a series of loops on face 22. Insulative yarn 18, in a preferred embodiment, is the same yarn as described in FIG. 1 as 200 denier texturized nylon plaited over 184 denier bare spandex. Similarly, electrically conductive yarn 20 in FIG. 3 is the same yarn as was described in FIG. 1 for fabric 10 being two ends of Bekitex BK 50/1 yarn plaited over 184 denier bare spandex. FIG. 3 shows a series of needles 26 on a first level forming a series of interlocking loops on the face 22 and another set of needles 28 on a second level performing a series of interlocking loops on the back 24. Thus, FIG. 3 represents the needle set-up required to knit the preferred structure of the fabric 10. It is contemplated that a 10-cut border machine with at least two color vertical stripe capability be utilized. It is also preferred that the fabric 10 be knitted with approximately 29 needles 26 and 29 needles 28. Approximately this number of needles will provide a fabric of a suitable width so that the fabric can be fashioned into a wrist strap. It is preferred that the tensions be adjusted to obtain a relaxed width of 7/8ths of an inch with 42–44 stitches per inch. The relaxed weight per yard of the resulting fabric 10 will be approximately 6/10ths of an ounce. Utilizing the yarns and the fibers suggested, the preferred embodiment results in a fabric 10 with approximately 49%, percentage by weight, texturized nylon, approximately 33% Bekitex BK yarn and approximately 18% spandex. The needle set-out illustrated in FIG. 3 illustrates insulative fiber 18 being looped around two of the needles 28 on the back 24 surface then being looped around one of the needles 26 on the face 22 surface before again being wrapped around two of the needles 28 on the back 24 surface. The needle set-out illustrated in FIG. 3 also illustrates electrically conductive yarn 20 forming loops around every other one of the needles 26 forming the face 22 surface. The needle set-out illustrated in FIG. 3 is of course only a preferred embodiment. There, of course, will exist many other needle set-outs which will result in a fabric 10 having the desired electrically conductive and elastic characteristics. It is not necessary, for example, that two levels of the needles be utilized nor that the exact spacing of the loops around the needles be maintained. It is also contemplated that while 29 face needles 26 and 29 back needles 28 are contemplated for the fabric 10, that in a preferred embodiment an edge may be constructed on each side by having a further number of both face needles 26 and back needles 28 around which are looped only the insulative fiber 18.

FIG. 4 illustrates an explosion view of the connector 12 connecting two ends of the fabric 10. The connector 12 is illustrated having a body 30 which receives the two ends of the fabric 10 and which has a plurality of projections 32 to grip the fabric 10 and hold it in place once the cover 34 is attached. The cover 34 is mated to the body 30 and held with a snap connector consisting of elements 36 and 38. These components then result in a connector 12 which provides both the mechanical and electrical connection required to the fabric 10 to form it into a closed loop and to conduct the electrostatic charge accumulation from the body of the individual wearer. Of course, many other mechanical and electrical connectors are envisioned and could be utilized. Specifically it is envisioned that separate mechanical and electrical connectors could be utilized on a single body strap.

The electrically conductive yarn 20, illustrated in FIG. 3, comprises a double end of Bekitex BK 50/1 yarn plaited over 184 denier bare spandex. The plaiting generally preferred is less than one turn per inch. Easier plaiting may also be achieved by stretching the spandex from its relaxed length and in one preferred embodiment is plaited with the spandex being stretched to at least double its relaxed length. The resulting fabric 10 in a length generally suitable for encompassing the wrist utilizing the electrically conductive fabric 10 will have an electrical surface resistivity of not more than $10^8$ ohms per square and generally $10^4$ ohms per square or less is preferred. The resulting body strap 16 should then have an overall resistance to ground of not more than $10^8$ ohms including the electric shock preventive resistor (not shown) included in the ground cord 14.

A body strap 16 constructed in the foregoing manner from the fabric 10 will result in a superior body strap which is sufficiently conductive, fits snug around the body and maintains a good electrical contact with the skin of the wearer, is readily expansible to easily fit into place, e.g. easily slips over the hand, maintains its elasticity over repeated usage, and is comfortable to the individual wearer, i.e. breathable.

It is contemplated that the fabric 10 can also be utilized for applications other than body straps. It is contemplated that the fabric 10 could be used for fabrics where electrical conductivity and elasticity are desired. Examples of contemplated uses include clothing, draperies, surgical gowns and other medical applications.

Thus, it can be seen that there has been shown and described a novel fabric and body strap having both electrical conductivity and elasticity. It is to be understood, however, that various changes, modifications, and substitutions in the form of the details of the described fabric and body strap can be made by those skilled in the art without departing from the scope of the invention as defined by the following claims:

What is claimed is:

1. A conductive body strap, comprising:
 a fabric having at least one interlaced yarn, said yarn including an end having an electrically conductive fiber plaited with an end having an elastomeric fiber;
 mechanical connection means coupled to said fabric for forming said fabric into a closed loop with an inside surface adapted to contact the body; and
 electrical connection means coupled to said fabric for contacting said electrically conductive fiber and for providing a connection point for an electrical cable capable of connecting said conductive body strap to ground;

whereby said conductive body strap has both elasticity and electrical conductivity.

2. A conductive body strap as in claim 1 wherein said at least one yarn is interlaced to form a series of interlocking loops.

3. A conductive body strap as in claim 2 wherein said at least one yarn is knitted.

4. A conductive body strap as in claim 1 wherein said electrically conductive fiber comprises a blend of staple stainless steel fibers and textile fibers and wherein said elastomeric fiber comprises spandex.

5. A conductive body strap, comprising:
a fabric having an electrically conductive yarn and an insulative yarn, said electrically conductive yarn and said insulative yarn being interlaced together to form a series of interlocking loops, wherein said electrically conductive yarn includes an end having an electrically conductive fiber, wherein said insulative yarn includes an end having an insulative fiber, and wherein at least one of said end having an electrically conductive fiber and said end having an insulative fiber is plaited with an end having an elastomeric fiber;
mechanical connection means coupled to said fabric for forming said fabric into a closed loop with an inside surface adapted to contact the body; and
electrical connection means coupled to said fabric for contacting said electrically conductive yarn and for providing a connection point for an electrical cable capable of connecting said conductive body strap to ground;
whereby said conductive body strap has both elasticity and electrical conductivity.

6. A conductive body strap as in claim 5 wherein said electrically conductive yarn is present on said inside surface.

7. A conductive body strap as in claim 5 wherein said electrically conductive yarn and said insulative yarn are knitted together.

8. A conductive body strap as in claim 5 wherein said end having an electrically conductive fiber is plaited with an end having an elastomeric fiber and said end having an insulative fiber is plaited with an end having an elastomeric fiber.

9. A conductive body strap as in claim 8 wherein said end having an elastomeric fiber is stretched during plaiting with said end having an electrically conductive fiber and said end having an insulative fiber.

10. A conductive body strap as in claim 9 wherein said end having an elastomeric fiber is stretched at least double its relaxed length during plaiting with said end having an electrically conductive fiber and said end having an insulative fiber.

11. A conductive body strap as in claim 5 wherein said electrically conductive fiber comprises a stainless steel fiber.

12. A conductive body strap as in claim 5 wherein said insulative fiber comprises nylon.

13. A conductive body strap as in claim 5 wherein said elastomeric fiber comprises spandex.

14. A conductive body strap as in claim 5 wherein said electrically conductive fiber comprises a blend of textile fibers and staple stainless steel fibers.

15. A conductive body strap as in claim 5 wherein said electrically conductive yarn and said insulative yarn are knitted together on a face and a back, said insulative yarn forming interlocking loops on both said face and said back, and said electrically conductive yarn forming interlocking loops only on said face.

* * * * *